United States Patent [19]

Midha et al.

[11] Patent Number: 5,565,193
[45] Date of Patent: Oct. 15, 1996

[54] HAIR STYLING COMPOSITIONS CONTAINING A SILICONE GRAFTED POLYMER AND LOW LEVEL OF A VOLATILE HYDROCARBON SOLVENT

[75] Inventors: Sanjeev Midha, Blue Ash; Peter M. Torgerson, Washington Court House; Christine Hall, Cincinnati, all of Ohio

[73] Assignee: Procter & Gamble, Cincinnati, Ohio

[21] Appl. No.: 273,289

[22] Filed: Jul. 11, 1994

Related U.S. Application Data

[63] Continuation of Ser. No. 102,433, Aug. 5, 1993, abandoned.
[51] Int. Cl.$^6$ .............................. A61K 7/11; A61K 7/09
[52] U.S. Cl. ............................................ 424/70.12
[58] Field of Search ................... 424/71, 70.12, 424/47

[56] References Cited

U.S. PATENT DOCUMENTS

| | | | |
|---|---|---|---|
| 3,928,558 | 12/1975 | Cheesman et al. | 424/70 |
| 4,749,565 | 6/1988 | Grollier | 424/71 |
| 4,933,176 | 6/1990 | van Reeth | 424/70 |
| 4,983,377 | 1/1991 | Murphy et al. | 424/70 |
| 4,988,506 | 1/1991 | Mitra et al. | 424/78 |
| 5,021,477 | 6/1991 | Garbe et al. | 424/71 |
| 5,209,924 | 5/1993 | Garbe et al. | 424/71 |

Primary Examiner—Peter F. Kulkosky
Attorney, Agent, or Firm—David K. Dabbiere; Leonard W. Lewis; Anthony D. Sabatelli

[57] ABSTRACT

Provided hair styling compositions comprising: (a) from about 0.1% to about 15%, by weight, of a silicone grafted adhesive polymer, said polymer being characterized by an organic polymeric backbone having silicone macromers grafted to said backbone; (b) from about 0.5% to about 15%, by weight, of a hydrocarbon solvent selected from the group consisting of $C_{10}$–$C_{14}$ branched chain hydrocarbons, and mixtures thereof; (c) a polar solvent phase comprising from about 80% to about 98.9%, by weight of the composition, of a polar solvent selected from the group consisting of water and $C_2$–$C_3$ monohydric alcohols, and mixtures thereof, wherein said composition contains no more than about 15%, by weight, of $C_3$ monohydric alcohol; wherein said organic polymer backbone is soluble in said polar solvent phase, and said silicone macromers of said hair setting polymer are soluble in said hydrocarbon solvent and insoluble in said polar solvent. In preferred embodiments, the compositions hereof additionally comprise a plasticizer for the silicone grafted hair setting polymer. Especially preferred plasticizers include acetyl tri-$C_2$–$C_8$ alkyl citrates, particularly acetyl triethyl citrate.

30 Claims, No Drawings

HAIR STYLING COMPOSITIONS CONTAINING A SILICONE GRAFTED POLYMER AND LOW LEVEL OF A VOLATILE HYDROCARBON SOLVENT

This is a continuation of application Ser. No. 08/102,433, filed on Aug. 5, 1993, now abandoned.

TECHNICAL FIELD

The present invention relates to hair styling compositions containing a silicone organic polymer as a hair setting agent. More particularly, the present invention relates to hairs styling compositions containing a silicone grafted organic polymer, having an organic backbone that is soluble either in water, lower alkanol, or a mixture thereof, and further containing an insoluble hydrocarbon solvent.

BACKGROUND OF THE INVENTION

The desire to have the hair retain a particular shape is widely held. The most common methodology for accomplishing this is the application of a composition to dampened hair, after shampooing and/or conditioning, or to dry, styled hair. These compositions provide temporary setting benefits and they can be removed by water or by shampooing. The materials used in the compositions to provide the setting benefits have generally been resins and have been applied in the form of mousses, gels, lotions or sprays.

Many people desire a high level of style retention, or hold, from a hair spray composition. In typical hair sprays, hold is achieved by the use of resins, such as AMPHOMER$^R$, supplied by National Starch and Chemical Company, and GANTREZ$^R$ SP 225, supplied by GAF. In general, as hair hold for hair spray compositions is increased, the tactile feel of the hair becomes stiffer and hence, less desirable. It is desirable to provide hair spray products which could provide an improved combination of hair hold and hair feel characteristics.

Hair sprays have been conventionally formulated with high amounts of monohydric alcohol solvents, such as ethanol and isopropanol, and relatively low amounts of water since the presence of water adversely affects spray quality. However, it is now particularly desirable to formulate hair spray compositions with reduced levels of volatile organic compounds, such as ethanol, isopropanol, and other volatile materials, such as aerosol propellants. One way to do this is to increase the levels of water in the formulations. In doing so, it would be highly desirable to provide reformulated products which overcome the problems conventionally associated with the addition of water to hair spray products. In particular, higher levels of water can negatively impact hair feel.

Recently, it has become known to utilize silicone grafted organic backbone polymers as hair setting agents in hairspray compositions and other hair styling compositions, e.g. hair tonics, lotions, rinses, mousses, etc. Silicone grafted polymers can be used to make hair spray compositions which provide hair setting ability with improved hair feel, e.g., increased softness relative to conventional polymeric hair setting agents.

However, it remains desirable to improve the hair feel performance these silicone grafted polymers can provide at a particular level of hair hold, or conversely, to improve hair hold (after application and drying of such compositions) for a particular level of hair feel performance. It is an object of this invention to provide hair spray compositions, and other aqueous, alcohol, or hydroalcoholic-based hair setting solutions, containing silicone grafted organic backbone polymeric hair setting agents that provide such improved combinations of hair feel/hair hold performance.

It is a further object of this invention to provide hair setting compositions, as described above, that provide both improved hair feel and improved hair hold ability for a particular level of silicone grafted polymer in the composition.

It is yet a further object of this invention to provide compositions that meet the above objects for conventional volatile organic solvent level (conventional VOC) compositions, which typically contain greater than 80% of volatile organic compounds, as well as for reduced volatile organic solvent level (reduced VOC) compositions, i.e., compositions having 80% or less volatile organic solvents.

These and other benefits as may be apparent from the description below can be obtained by the present invention.

The present compositions can comprise, consist of, or consist essentially of any of the required or optional ingredients and/or limitations described herein.

All percentages and ratios are calculated on a weight basis unless otherwise indicated. All percentages are calculated based upon the total composition unless otherwise indicated.

All ingredient levels are refer to the active level of that ingredient, and are exclusive of solvents, by-products, or other impurities that may be present in commercially available sources, unless otherwise indicated.

SUMMARY OF THE INVENTION

The present invention relates to hair styling compositions comprising:

(a) from about 0.1% to about 15%, by weight, of a silicone grafted adhesive polymer, said polymer being characterized by an organic polymeric backbone having silicone macromers grafted to said backbone;

(b) from about 0.5% to about 15%, by weight, of a hydrocarbon solvent selected from the group consisting of $C_{10}$–$C_{14}$ branched chain hydrocarbons, and mixtures thereof, having a boiling point of from about 105° C. to about 260° C.;

(c) a polar solvent phase comprising from about 80% to about 98.9%, by weight of the composition, of a polar solvent selected from the group consisting of water and $C_2$–$C_3$ monohydric alcohols, and mixtures thereof, wherein said composition contains no more than about 15%, by weight, of $C_3$ monohydric alcohol;

wherein said organic polymer backbone is soluble in said polar solvent phase, and said silicone macromers of said hair setting polymer are soluble in said hydrocarbon solvent and insoluble in said polar solvent.

In preferred embodiments, the compositions hereof additionally comprise a plasticizer for the silicone grafted hair setting polymer. Especially preferred plasticizers include acetyl tri-$C_2$–$C_8$ alkyl citrates, particularly acetyl triethyl citrate.

DETAILED DESCRIPTION OF THE INVENTION

The essential components of the present invention are described below. Also included is a nonexclusive description of various optional and preferred components useful in embodiments of the present invention.

Silicone Grafted Adhesive Polymer

The compositions of the present invention essentially comprise a silicone grafted adhesive polymer as a hair setting agent. The compositions hereof will generally comprise from about 0.1% to about 15%, preferably from 0.5% to about 8%, more preferably from about 1% to about 8%, by weight of the composition, of the silicone grafted polymer. It is not intended to exclude the use of higher or lower levels of the polymers, as long as an effective amount is used to provide adhesive or film forming properties to the composition and the composition can be formulated and effectively applied for its intended purpose. By adhesive polymer what is meant is that when applied as a solution to a surface and dried, the polymer forms a film. Such a film will have adhesive and cohesive strength, as is understood by those skilled in the art.

The silicone grafted polymers are characterized by polysiloxane moieties covalently bonded to and pendant from a polymeric carbon-based backbone. The backbone will preferably be a carbon chain derived from polymerization of ethylenically unsaturated monomers, but can also be, cellulosic chains or other carbohydrate-derived polymeric chains to which polysiloxane moieties are pendant. The backbone can also include ether groups, i.e., C-O-C. The polysiloxane moieties can be substituted on the polymer or can be made by co-polymerization of polysiloxane-containing polymerizable monomers (e.g. ethylenically unsaturated monomers, ethers, and/or epoxides) with non-polysiloxane-containing polymerizable monomers.

The polysiloxane-grafted polymer should have a weight average molecular weight of at least about 20,000. There is no upper limit for molecular weight except that which limits applicability of the invention for practical reasons, such as processing, aesthetic characteristics, formulateability, etc. In general, the weight average molecular weight will be less than about 10,000,000, more generally less than about 5,000,000, and typically less than about 3,000,000. Preferably, the weight average molecular weight will be between about 50,000 and about 2,000,000, more preferably between about 75,000 and about 1,000,000, most preferably between about 100,000 and about 750,000.

Preferably, the grafted-polymers hereof when dried to form a film have a Tg or Tm of at least about −20° C., preferably at least about 20° C, so that they are not unduly sticky, or "tacky" to the touch. As used herein, the abbreviation "Tg" refers to the glass transition temperature of the non-polysiloxane backbone of the polymer, and the abbreviation "Tm" refers to the crystalline melting point of the non-siloxane backbone, if such a transition exists for a given polymer. Preferably, both the Tg and the Tm, if any, are above about −20° C., more preferably above about 20° C.

The silicone grafted polymers for the compositions of the present invention include "silicone-containing" (or "polysiloxane-containing") monomers, which form the silicone macromer pendant from the backbone, and non-silicone-containing monomers, which form the organic backbone of the polymer.

The silicone grafted polymers should satisfy the following four criteria:

(1) when dried the polymer phase-separates into a discontinuous phase which includes the polysiloxane portion and a continuous phase which includes the non-polysiloxane portion;

(2) the polysiloxane portion is covalently bonded to the non-polysiloxane portion; and (3) the molecular weight of the polysiloxane portion is at least about 500; and When used in a composition, such as a personal care composition for application to the hair or skin, the non-polysiloxane portion should permit the polymer to deposit on the intended surface, such as hair or skin.

It is believed that the phase separation property provides a specific orientation of the polymer which results in the desired combination of tactile feel, and film-forming or adhesive benefits. The phase-separating nature of the compositions of the present invention may be determined as follows:

The polymer is cast as a solid film out of a solvent (i.e., a solvent which dissolves both the backbone and the polysiloxane-graft portions). This film is then sectioned and examined by transmission electron microscopy. Microphase separation is demonstrated by the observation of inclusions in the continuous phase. These inclusions should have the proper size to match the size of the silicone chain (typically a few hundred nm or less) and the proper density to match the amount of silicone present. This behavior is well documented in the literature for polymers with this structure (see, for example, S. D. Smith, Ph.D. Thesis, University of Virginia, 1987, and references cited therein, said thesis incorporated by reference herein).

A second method for determining phase-separating characteristics involves examining the enrichment of the concentration of silicone at the surface of a polymer film relative to the concentration in the bulk polymer. Since the silicone prefers the low energy air interface, it preferentially orients on the polymer surface. This produces a surface with the silicone oriented at the surface of the film. This can be demonstrated experimentally by ESCA (electron spectroscopy for chemical analysis) of the dried film surface. Such an analysis shows a high level of silicone and a greatly reduced level of backbone polymer when the film surface is analyzed. (Surface here means the first few tens of Angstroms of film thickness.) By varying the angle of the interrogating beam the surface can be analyzed to varying depths.

A third method for determining phase-separating characteristics is via Scanning Electron Microscopy (SEM), to examine the topographical morphology of dried film of the silicone grafted polymer. SEM can be used to demonstrate microphase separation at the surface of the polymer film by the observation of hemi-spherical discontinuities (typically hemispherical or hemi-conical) formed by the silicone macromer component grafted on the polymer backbone of the silicone grafter polymer.

The preferred silicone grafted polymers comprise an organic backbone preferably a carbon backbone derived from ethylenically unsaturated monomers, such as a vinyl polymeric backbone, and a polysiloxane macromer (especially preferred are polydialkylsiloxane, most preferably polydimethylsiloxane) grafted to the backbone. The polysiloxane macromer should have a weight average molecular weight of at least about 500, preferably from about 1,000 to about 100,000, more preferably from about 2,000 to about 50,000, most preferably about 5,000 to about 20,000. Organic backbones contemplated include those that are derived from polymerizable, ethylenically unsaturated monomers, including vinyl monomers, and other condensation monomers (e.g., those that polymerize to form polyamides and polyesters), ring-opening monomers (e.g., ethyl oxazoline and caprolactone), etc. Also contemplated are backbones based on cellulosic chains, ether-containing backbones, etc.

Examples of useful polymers and how they are made are described in detail in U.S. Pat. No. 4,693,935, Mazurek, issued Sep. 15, 1987, U.S. Pat. No. 4,728,571, Clemens et al., issued Mar. 1, 1988, both of which are incorporated herein by reference.

Suitable silicone grafted polymers are also disclosed in EPO Application 90307528.1, published as EPO Application 0 408 311 A2 on Jan. 11, 1991, Hayama, et al., U.S. Pat. No. 5,061,481, issued Oct. 29, 1991, Suzuki et al., U.S. Pat. No. 5,106,609, Bolich et al., issued Apr. 21, 1992, U.S. Pat. No. 5,100,658, Bolich et al., issued Mar. 31, 1992, U.S. Pat. No. 5,100,657, Ansher-Jackson, et al., issued Mar. 31, 1992, U.S. Pat. No. 5,104,646, Bolich et al., issued Apr. 14, 1992, U.S. Ser. No. 07/758,319, Bolich et al, filed Aug. 27, 1991, and U.S. Ser. No. 07/758,320, Torgerson et al., filed Aug. 27, 1991, all of which are incorporated by reference herein.

The preferred silicone grafted polymers are comprised of monomer units derived from: at least one free radically polymerizable ethylenically unsaturated monomer or monomers and at least one free radically polymerizable polysiloxane-containing ethylenically unsaturated monomer or monomers.

The silicone grafted polymers hereof generally comprise from about 1% to about 50%, by weight, of polysiloxane-containing monomer units, i.e., monomer units polysiloxane-containing monomers (referred to herein as "C" monomers), and from about 50% to about 99% by weight, of non-polysiloxane-containing monomers.

The non-polysiloxane-containing monomer units can be derived from polar, or hydrophilic, monomers, "A" monomers, or mixtures of polar hydrophilic monomers and low polarity, or hydrophobic, "B" monomers.

Hydrophobic monomers means monomers which form substantially water insoluble homopolymers. Hydrophilic monomers means monomers which do not form substantially water insoluble homopolymers. Substantially water soluble shall refer to monomers that form homopolymers that are soluble in distilled (or equivalent) water, at 25° C., at a concentration of 0.2% by weight, and are preferably soluble at 1.0% by weight. Substantially water insoluble shall refer to monomers that form homopolymers that are not soluble in distilled (or equivalent) water, at 25° C., at a concentration of 0.2% by weight, and preferably not soluble at 0.1% by weight. The weight average molecular weight for purposes of determining substantial water solubility or insolubility shall be about 100,000, although solubility at higher molecular weight shall also be indicative of solubility at about 100,000.

The particular relative amounts of A, B, and C monomers can vary as long as the polymer backbone is soluble in the polar solvent hereof and the silicone grafted copolymer exhibits phase separation when dried.

Representative examples of A monomers include acrylic acid, methacrylic acid, N,N-dimethylacrylamide, dimethyl aminoethyl methacrylate, quaternized dimethylaminoethyl methacrylate, methacrylamide, N-t-butyl acrylamide, maleic acid, maleic anhydride and its half esters, crotonic acid, iraconic acid, acrylamide, acrylate alcohols, hydroxyethyl methacrylate, diallyldimethyl ammonium chloride, vinyl pyrrolidone, vinyl ethers (such as methyl vinyl ether), maleimides, vinyl pyridine, vinyl imidazole, other polar vinyl heterocyclics, styrene sulfonate, allyl alcohol, vinyl alcohol (such as that produced by the hydrolysis of vinyl acetate after polymerization), vinyl caprolactam, salts of any acids and amines listed above, and mixtures thereof. Preferred A monomers include acrylic acid, N,N-dimethyl acrylamide, dimethylaminoethyl methacrylate, quaternized dimethyl aminoethyl methacrylate, vinyl pyrrolidone, salts of acids and amines listed above, and mixtures thereof.

Representative examples of B monomers are acrylic or methacrylic acid esters of $C_1$–$C_{18}$ alcohols, such as methanol, ethanol, methoxy ethanol, 1-propanol, 2-propanol, 1-butanol, 2-methyl-1propanol, 1-pentanol, 2-pentanol, 3-pentanol, 2-methyl-1-butanol, 1-methyl-1-butanol, 3-methyl-1-butanol, 1-methyl-1-pentanol, 2-methyl-1-pentanol, 3-methyl-1-pentanol, t-butanol(2-methyl-2-propanol), cyclohexanol, neodecanol, 2-ethyl-1-butanol, 3-heptanol, benzyl alcohol, 2-octanol, 6-methyl-1-heptanol, 2-ethyl-1-hexanol, 3,5-dimethyl-1-hexanol, 3,5,5-tri methyl-1-hexanol, 1-decanol, 1-dodecanol, 1-hexadecanol, 1-octa decanol, and the like, the alcohols having from about 1–18 carbon atoms with the number of carbon atoms preferably being from about 1–12; styrene; polystyrene macromer; vinyl acetate; vinyl chloride; vinylidene chloride; vinyl propionate; alpha-methylstyrene; t-butylstyrene; butadiene; cyclohexadiene; ethylene; propylene; vinyl toluene; and mixtures thereof. Preferred B monomers include n-butyl methacrylate, isobutyl methacrylate, t-butyl acrylate, t-butyl methacrylate, 2-ethylhexyl methacrylate, methyl methacrylate, and mixtures thereof. Most preferably, B is selected from t-butyl acrylate, t-butyl methacrylate, and mixtures thereof.

Polymerizable polysiloxane-containing monomers (C monomer) are exemplified by the general formula:

$$X(Y)_n Si(R)_{3-m} Z_m$$

wherein X is an ethylenically unsaturated group copolymerizable with the A and B monomers, such as a vinyl group; Y is a divalent linking group; R is a hydrogen, hydroxyl, lower alkyl (e.g. $C_1$–$C_4$), aryl, alkaryl, alkoxy, or alkylamino; Z is a monovalent siloxane polymeric moiety having a number average molecular weight of at least about 500, is essentially unreactive under copolymerization conditions, and is pendant from the vinyl polymeric backbone described above; n is 0 or 1; and m is an integer from 1 to 3. C has a weight average molecular weight as described above. Preferably, the C monomer has a formula selected from the following group:

$$X-\overset{O}{\underset{\|}{C}}-O-(CH_2)_q-(O)_p-Si(R^1)_{3-m}Z_m$$

In this structure, m is 1, 2 or 3 (preferably m=1); p is 0 or 1; q is an integer from 2 to 6; $R^1$ is hydrogen, hydroxyl, lower alkyl, alkoxy, alkylamino, aryl, or alkaryl (preferably $R^1$ is alkyl); X is $$\underset{R^2}{\overset{CH=C-}{|}} \underset{R^3}{\overset{|}{}}$$

$R^2$ is hydrogen or —COOH (preferably $R^2$ is hydrogen); $R^3$ is hydrogen, methyl or —$CH_2COOH$ (preferably $R^3$ is methyl); Z is $$R^4 \!\!-\!\!\left(\!\!\underset{R^6}{\overset{R^5}{\underset{|}{\overset{|}{Si}}}}\!\!-\!\!O\!\!-\!\!\right)\!\!r;$$

$R^4$, $R^5$, and $R^6$ independently are lower alkyl, alkoxy, alkylamino, aryl, arkaryl, hydrogen or hydroxyl (preferably $R^4$, $R^5$, and $R^6$ are alkyls); and r is an integer of about 5 or higher, preferably about 10 to about 1500 (most preferably r is from about 100 to about 250). Most preferably, $R^4$, $R^5$, and $R^6$ are methyl, p=0, and q=3.

In general, the silicone grafted polymer will preferably comprise from about 50% to about 99%, more preferably from about 60% to about 98%, most preferably from about 75% to about 95%, by weight of the polymer, of non-silicone macroruer-containing monomer units, e.g. the total A and B monomer units, and from about 1% to about 50%, preferably from about 1% to about 40%, more preferably from about 2% to about 25%, of silicone macromer-containing monomer units, e.g. the C monomer units. The level of A monomer units can be from about 1% to about 99%, preferably from about 5% to about 80%, more preferably from about 10% to about 50%, most preferably from about 15% to about 40%; the level of B monomer units, can be from 0% to about 99%, preferably from about 1% to about 90%, more preferably from about 5% to about 85%, most preferably from about 15% to about 80%; and the level of C monomer units, from about 1% to about 50%, preferably from about 1% to about 40%, more preferably from about 2% to about 25%.

The composition of any particular silicone grafted polymer will help determine its formulational properties. By appropriate selection and combination of particular A, B and C components, the silicone grafted polymer can be optimized for inclusion in specific vehicles. The backbone of the silicone grafted polymer included in the compositions hereof must be soluble in the polar solvent, which is hereinafter referred to as the silicone grafted polymer, as a whole, being soluble in the polar solvent. This is determined according to whether the polymer can stay in solution or precipitates out of solution at 25° C. at the concentration present in the composition or whether the range of concentrations for silicone grafted polymer discribed herein. It is well within the skill of one in the art to select monomers for incorporation into the polymers for formulateability and solubility in selected polar solvent systems.

Exemplary silicone grafted polymers for use in the present invention include the following:

(i) acrylic acid/n-butylmethacrylate/polydimethylsiloxane (PDMS) macromer 20,000 molecular weight macromer (ii) dimethylaminoethyl methacrylate/isobutyl methacrylate/2--ethylhexyl-methacrylate/PDMS macromet-20,000 molecular weight macromer (iii) t-butylacrylate/acrylic acid/PDMS macromer-10,000 molecular weight macromer (iv) t-butylacryylate/acrylic acid/PDMS macromer-20,000 molecular weight macromer The silicone grafted polymers can be synthesized by free radical polymerization of the polysiloxane-containing monomers with the non-polysiloxane-containing monomers. The general principles of free radical polymerization methods are well understood. See, for example, Odian, "Principles of Polymerization", 2nd edition, John Wiley & Sons, 1981, pp. 179–318. The desired monomers are all placed in a reactor, along with a sufficient amount of a mutual solvent so that when the reaction is complete the viscosity of the reaction is reasonable. Typical monomer loadings are from about 20% to about 50%. Undesired terminators, especially oxygen, are removed as needed. This is done by evacuation or by purging with an inert gas, such as argon or nitrogen. The initiator is introduced and the reaction brought to the temperature needed for initiation to occur, assuming thermal initiators are used. Alternatively, redox or radiation initiation can be used. The polymerization is allowed to proceed as long as needed for a high level of conversion to be achieved, typically from a few hours to a few days. The solvent is then removed, usually by evaporation or by precipitating the polymer by addition of a nonsolvent. The polymer can be further purified, as desired.

In particular the silicone grafted polymers can be purified by removing unreacted silicone-containing monomer and silicone macromer-grafted polymer with viscosities at 25° C. of about 10,000,000 centistokes and less. This can be done, for the example, by hexane extraction. After drying the resin from its reaction solvent hexane extraction of the reaction product can be performed by adding an excess of hexane to the reaction product and heating to near the Tg of the non-silicone portion of the polymer. The mixture is held at this temperature with stirring for about 30 minutes and cooled to room temperature. The hexane is removed by vacuum suction. Two more hexane extraction cycles are preferably conducted in the same manner as above. After the third cycle, residual hexane remaining with the product is removed by distillation and vacuum drying.

As an alternative to a batch reaction, the silicone grafted polymer can be made by a semi-continuous or continuous process. In the semi-continuous process, two or more additions of monomers is made during the polymerization reaction. This is advantageous when the polymer is made of several monomers which react during the polymerization at different rates. The proportions of monomers added to the reaction at the separate points of addition can be adjusted by one of ordinary skill in the art such that the polymers of the final product have a more uniform structure. In other words, the polymers of the final product will have a more consistent monomer content distribution for each of the monomer types charged to the reaction. Typically, the silicone macromer-combining monomers, the "C" monomers as described above, well react more slowly than the non-silicone macromer-containing monomers. To compensate for this, for example, more consistent distribution of C monomer can be obtained by adding all the C monomer and half of the A and B monomers in the first addition of monomers to the reaction, and the rest of the A and B monomers in a second addition.

As is known in the art, polymers which have acidic functionalities, such as carboxyl groups, are usually used in at least partially neutralized form to promote solubility/dispersibility of the polymer. In addition, use of the neutralized form aids in the ability of the hair care compositions to be removed from the hair by shampooing. In general, it is preferred that from about 10% to 100%, more preferably from about 20% to about 90%, even more preferably from about 40% to about 85%, of the acidic monomers of the polymer be neutralized.

Any conventionally used base, organic or metallic, may be used for neutralization of the polymers. Metallic bases are particularly useful in the present compositions. Hydroxides, where the cation is an alkali metal or an alkaline earth metal, are suitable neutralizers for use in the present hair spray compositions.

Preferred neutralizing agents for use in hair spray compositions of the present invention are potassium hydroxide and sodium hydroxide.

Examples of other suitable neutralizing agents which may be included in the hair spray compositions of the present invention include amines, especially amino alcohols such as 2-amino-2-methyl-1,3-propanediol (AMPD), 2-amine-2-ethyl-1,3-propanediol (AEPD), 2-amino-2-methyl-1-propanol (AMP), 2-amino-1-butanol (AB), monoethanolamine (MEA), diethanolamine (DEA), triethanolamine (TEA), monoisopropanolamine (MIPA), diisopropanol-amine (DIPA), tri-isopropanolamine (TIPA) and dimethyl steramine (DMS). Particularly useful neutralizing agents are mixtures of amines and metallic bases.

Polymers having basic functionalities, e.g., amino groups, are preferably at least partially neutralized with an acid, e.g., hydrogen chloride.

Solubility of the silicone grafted polymer, as described above, should be determined after neutralization, if any, as well as after addition of other ingredients that may be included in the polar solvent phase, such as surfactants, solubilizers, etc.

Polar Solvent Phase

The liquid care compositions of the present invention also include a polar solvent phase as a liquid vehicle for the silicone grafted polymer. The polar solvent phases comprise one or more polar solvents that are present in the hair care compositions at a level of from about 80% to about 98.9%, preferably from about 85% to about 98%, more preferably from about 90% to about 95% of the total composition.

The polar solvents essential to the present compositions are selected from the group consisting of water $C_2$-$C_3$ monohydric alkanols, and mixtures thereof. If present, $C_3$ alkanols, such as isopropanol, should be used at levels no greater than about 15% by weight of the composition, preferably no greater than about 12%, more preferably no greater than about 10%. High levels of $C_3$ monohydric alcohols are undesirable in the present compositions due to potential odor issues they can create. Preferred polar solvent phases contain water, ethanol, or mixtures thereof.

Where water and alcohol mixtures are used, for instance, water-ethanol or wateroisopropanol-ethanol, the water content of the compositions is generally in the range of from about 0.5% to about 99%, preferably from about 5% to about 50% by weight of the total composition. In such mixtures, the alcohol solvents are generally present in the range of from 0.5% to about 99%, preferably from about 50% to about 95%, by weight of the total composition.

In yet another aspect of this invention are provided hair styling products, such as hair spray compositions, which contain reduced levels of volatile organic solvents. A reduced volatile organic solvent hair spray composition of the present invention contains no more than 80% volatile organic solvents (which include, for example, alkanols but not water). As used herein, volatile organic solvents means solvents which have at least one carbon atom and exhibit a vapor pressure of greater than 0.1 mm Hg at 20° C.

In the reduced volatile organic solvent hair styling products hereof, the compositions generally comprise at least 10%, by weight, of water. It is also specifically contemplated that they may contain at least about 11%, 12%, 13%, 14%, 15%, or more water.

The reduced volatile organic solvent compositions hereof will comprise up to about 90%, preferably up to about 70%, more preferably up to about 60% even more preferably no more than about 50%, water; and from about 10% to about 80%, preferably from about 20% to about 80%, more preferably from about 40% to about 80%, of volatile organic solvent. It is also contemplated that the compositions can be limited to containing no more than about 75%, 65%, 55%, or other levels of volatile organic solvents.

Nonpolar, Branched Chain Hydrocarbon

The compositions hereof contain as an essential element a volatile, nonpolar, branched chain hydrocarbon, which acts as a solvent for the silicone portion of the silicone grafted copolymer and is safe for topical application to the skin and hair. The branched chain hydrocarbon solvent hereof is present at a level of from about 0.5% to about 15%, preferably from about 1% to about 10%, more preferably from about 2% to about 8%, by weight of the composition.

The branched chain hydrocarbon solvent is characterized by a boiling point of at least about 105° C., preferably at least about 110° C, more preferably at least about 125° C., most preferably at least about 150 ° C. The boiling point is also generally about 260° C. or less, preferably about 200° C. or less. The hydrocarbon chosen should also be safe for topical application to the hair and skin.

The branched chain hydrocarbon solvents are selected from the group consisting of $C_{10}$-$C_{14}$ branched chain hydrocarbons, and mixtures thereof, preferably $C_{11}$-$C_{13}$ branched chain hydrocarbons, more preferably $C_{12}$ branched chain hydrocarbons. Saturated hydrocarbons are preferred, although it isn't necessarily intended to exclude unsaturated hydrocarbons.

Examples of suitable nonpolar solvents include isoparaffins of the above chain sizes. Isoparaffins are commercially available from Exxon Chemical Co. Examples include Isopar$^{TM}$ G ($C_{10}$-$C_{11}$ isoparaffins), isopar$^{TM}$ H and K ($C_{11}$-$C_{12}$ isoparaffins), and Isopar$^{TM}$ L ($C_{11}$-$C_{13}$ isoparaffins). The most preferred nonpolar solvent are $C_{12}$ branched chain hydrocarbons, especially isododecane. Isododecane is commercially available from Preperse, Inc. (South Plainfield, N.J., USA) as Permethyl$^{TM}$99A.

The silicone macromer portion of the silicone grafted polymer is soluble in the nonpolar hydrocarbon solvent in the present compositions. This can be easily determined by verifying whether a silicone macromer of the same composition and molecular weight as that grafted to the silicone grafted polymer is soluble in the nonpolar hydrcarbon solvent. In general, the macromer should be soluble at 25° C. at a concentration of 0.1% by weight of the hydrocarbon solvent, preferably at 1%, more preferably at 5%, most preferably at 15%.

The nonpolar hydrocarbon solvent, however, is insoluble in the polar solvent of the composition. This is determined in the absence of the silicone grafted polymer, or other emulsifying agents, and can easily be verified by observing whether the polar and nonpolar solvents form separate phases after being mixed together.

Without intending to be necessarily limited by any particular theory, it is believed that the nonpolar hydrocarbon solvent solubilizes the silicone macromer portion of the silicone grafted polymer. This is believed to aid in obtaining a smoother polymer film upon drying. Since the hydrocarbon solvent is less volatile than the polar solvent phase, the hydrocarbon solvent maintains the silicone portions in solubilized form for a relatively long period as the composition dries, thus minimizing aggregation of the silicone portions and, therefore, allowing the polymer to dry as a smoother film.

Plasticizer

The compositions hereof can optionally contain a plasticizer for the silicone grafted polymer. Any plasticizer suitable for use in hair care products or for topical application to the hair or skin can be used. A wide variety of plasticizers are known in the art. These include glycerin, diisobutyl adipate, butyl stearate, and propylene glycol. Plasticizers are typically used at levels of from about 0.01% to about 10%, by weight of the composition, preferably from about 0.05% to about 3%, more preferably from about 0.05% to about 1%.

In a highly preferred embodiment hereof, surprising improvements in hair hold performance can be obtained when the present compositions have included therein certain plasticizers selected from the group consisting of acetyl tri-$C_2$–$C_8$ alkyl citrates, such as acetyl triethyl citrate. Other suitable examples include the tri-propyl, -butyl, -pentyl, etc., analogues of acetyl triethyl citrate.

Whereas it has been found that plasticizers of this type result in a brittle, gritty film of the silicone grafted polymer when formed from a composition not including the hydrocarbon solvent of the present invention, the use of the acetyl tri-alkyl citrate in the presence of the hydrocarbon solvent in the present compositions can provide improved hair hold relative to the citrate-free composition, without causing the hair to feel brittle or gritty, and while also allowing the hair to exhibit improved softness and comb-ability relative to a citrate plasticizer-containing composition that does not contain the nonpolar hydrocarbon solvent hereof.

The acetyl tri-alkyl citrate plasticizer hereof is generally used at a level of from about 0.025% to about 2%, preferably from about 0.05% to about 1%, by weight of the composition. Preferably, the weight ratio of silicone grafted polymer to the acetyl tri-alkyl citrate is from about 1:1 to about 40:1, preferably from about 10:1 to about 30:1, more preferably from about 15:1 to about 25:1.

Optional Ingredients

The present compositions can contain a wide variety of optional ingredients, including among them any of the types of ingredients known in the art for use in hair setting compositions, especially hair spray compositions and hair setting tonics. These ingredients include, but are not limited to, surfactants (including fluorinated surfactants and silicone copolyols, and silicone tonic strength modifiers, non-silicone grafted film-forming polymers, propellants, hair conditioning agents (e.g., silicone fluids, fatty esters, fatty alcohols, long chain hydrocarbons, cationic surfactants, etc.)

Fluorosurfactants

Fluorosurfactants useful in the present compositions include perfluorinated compounds which can be represented by the formula

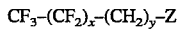

where Z is a water solubilizing group of either organic or inorganic character, x is an integer which is generally from 2 to 17, particularly from 7 to 11, and y is an integer from 0 to 4, and said compounds may be cationic, anionic, amphoteric or zwitterionic, depending upon the nature of the grouping or groupings encompassed by Z. The Z groups may be or may comprise sulfate, sulfonate, carboxylate, amine salt, quaternary ammonium, phosphate, phosphonate, and combinations thereof. The perfluorinated compounds are known in the art. These compounds are described in U.S. Pat. No. 4,176,176, Cella et al., issued Nov. 27, 1979; U.S. Pat. No. 3,993,745, Cella et al., issued Nov. 23, 1976, and U.S. Pat. No. 3,993,744, Cella et al., issued Nov. 23, 1976, each being incorporated herein by reference.

Suitable anionic fluorosurfactants can have anionic moieties which include carboxylates, sulfates, sulfonates, phosphonates and phosphates or any combination thereof. Counterions therefore can include sodium, $NH_4$, magnesium, potassium, tri-ethanolamine, di-ethanolamine, and similar moieties. Suitable cationic fluorosurfactants can have cationic moieties which include quaternary ammonium compounds where the counterions can be chloride or any other halide, methosulfate, ethosulfate, phosphate, acetate, and other similar moieties. Also, suitable cationic fluorosurfactants can have cationic moieties which include primary, secondary and tertiary amine salts of acids such as hydrochloric, lactic, phosphoric, sulfuric and other similar acids.

Also suitable for use are amphoteric fluorosurfactants, such as Fluorad FC-100® supplied by 3M; and the experimental amphoteric fluorosurfactant L-12231 supplied by 3M; and also include zwitterionic fluorosurfactants such as those conforming to the formula $R_fCH_2CH(OCOCH_3)CH_2N^+(CH_3)_2CH_2CO_2^-$ wherein $R_f=F(CF_2CF_2)_{3-8}$ such as Zonyl FSK® supplied by DuPont.

Fluorosurfactant, are typically used at levels of from about 0.01% to about 2%, preferably from about 0.01% to about 1.5%. More preferably from about 0.02% to about 1%.

Non-fluorinated Surfactants

Optionally, the hair spray compositions can contain one or more non-fluorinated surfactant. Generally, if used such non-fluorinated surfactants will be used at a total level of from about 0.01% to about 2%, preferably from about 0.01% to about 1.5% and more preferably from about 0.01% to about 1%, by weight of the composition.

A wide variety of non-fluorinated surfactants can be used, including anionic, cationic, amphoteric, and zwitterionic surfactants.

Anionic surfactants include, for example: alkyl and alkenyl sulfates; alkyl and alkenyl ethoxylated sulfates; (preferably having an average degree of ethoxylation of 1 to 10), succinamate surfactants, such as alkylsulfosuccinamates and dialkyl esters of sulfosuccinic acid; neutralized fatty acid esters of isethionic acid; and alkyl and alkenyl sulfonates, including, for example, olefin sulfonates and beta-alkoxy alkane sulfonates. Preferred are alkyl and alkenyl sulfates and alkyl and alkenyl ethoxylated sulfates such as the sodium and ammonium salts of $C_{12}$–$C_{18}$ sulfates and ethoxylated sulfates with a degree of ethoxylation of from 1 to about 6, preferably from 1 to about 4, e.g., lauryl sulfate and laureth (3.0) sulfate.

Amphoteric surfactants include those which can be broadly described as derivatives of aliphatic secondary and tertiary amines in which the aliphatic radical can be straight chain or branched and wherein one of the aliphatic substituents contains from about 8 to about 18 carbon atoms and one contains an anionic water solubilizing group, e.g., carboxy, sulfonate, sulfate, phosphate, or phosphonate. Examples of compounds falling within this definition are sodium 3-dodecylaminopropionate, N-alkyltaurines such as the one prepared by reacting dodecylamine with sodium isethionate according to the teaching of U.S. Pat. No. 2,658,072, N-higher alkyl aspartic acids such as those produced according to the teaching of U.S. Pat. No. 2,438,091, and the products sold under the trade name "Miranol" and described in U.S. Pat. No. 2,528,378. Others include alkyl, preferably $C_6$–$C_{22}$ and most preferably $C_8$–$C_{12}$, amphoglycinates; alkyl, preferably $C_6$–$C_{22}$ and most preferably $C_8$–$C_{12}$, amphopropionates; and mixtures thereof.

Suitable zwitterionic surfactants for use in the present compositions can be exemplified by those which can be broadly described as derivatives of aliphatic quaternary ammonium, phosphonium, and sulfonium compounds, in which the aliphatic radicals can be straight chain or branched, and wherein one of the aliphatic substituents contains from about 8 to 18 carbon atoms and one contains an anionic water-solubilizing group, e.g., carboxy, sulfonate, sulfate, phosphate, or phosphonate. A general formula for these compounds is:

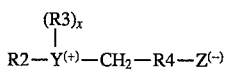

wherein R2 contains an alkyl, alkenyl, or hydroxy alkyl radical of from about 8 to about 18 carbon atoms, from 0 to about 10 ethylene oxide moieties and from 0 to 1 glyceryl moiety; Y is selected from the group consisting of nitrogen, phosphorus, and sulfur atoms; R3 is an alkyl or monohydroxyalkyl group containing 1 to about 3 carbon atoms; x is 1 when Y is sulfur or phosphorus, 1 or 2 when Y is nitrogen; R4 is an alkylene or hydroxyalkylene of from 1 to about 4 carbon atoms and Z is a radical selected from the group consisting of carboxylate, sulfonate, sulfate, phosphonate, and phosphate groups. Classes of zwitterionics include alkyl amino sulfonates, alkyl betaines, and alkyl amido betaines.

Cationic surfactants useful in compositions of the present invention contain amino or quaternary ammonium hydrophilic moieties which are positively charged when dissolved in the aqueous composition of the present invention. Cationic surfactants among those useful herein are disclosed in the following documents, all incorporated by reference herein: M. C. Publishing Co., McCutcheon's, Detergents & Emulsifiers, (North American edition 1979); Schwartz, et al., Surface Active Agents, Their Chemistry and Technology, New York: Interscience Publishers, 1949; U.S. Pat. No. 3,155,591, Hilfer, issued Nov. 3, 1964; U.S. Pat. No. 3,929,678, Laughlin, et al., issued Dec. 30, 1975; U.S. Pat. No. 3,959,461, Bailey, et al., issued May 25, 1976; and U.S. Pat. No. 4,387,090, Bolich, Jr., issued Jun. 7, 1983.

Among the quaternary ammonium-containing cationic surfactant materials useful herein are those of the general formula:

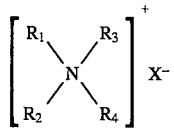

wherein $R_1$ is an aliphatic group of from 1 to 22 carbon atoms, or an aromatic, aryl or alkylaryl group having from 12 to 22 carbon atoms; $R_2$ is an aliphatic group having from 1 to 22 carbon atoms; $R_3$ and $R_4$ are each alkyl groups having from 1 to 3 carbon atoms, and X is an anion selected from halogen, acetate, phosphate, nitrate and alkylsulfate radicals. The aliphatic groups may contain, in addition to carbon and hydrogen atoms, ether linkages, and other groups such as amido groups. Other quaternary ammonium salts useful herein are diquaternary ammonium salts.

Salts of primary, secondary and tertiary fatty amines are also suitable cationic surfactants for use herein. The alkyl groups of such amines preferably have from 12 to 22 carbon atoms, and may be substituted or unsubstituted. Secondary and tertiary amines are preferred, tertiary amines are particularly preferred. Such amines, useful herein, include stearamido propyl dimethyl amine, diethyl amino ethyl stearamide, dimethyl stearamine, dimethyl soyamine, soyamine, myristyl amine, tridecyl amine, ethyl stearylamine, N-tallowpropane diamine, ethoxylated (5 moles E.O.) stearylamine, dihydroxy ethyl stearylamine, and arachidylbehenylamine. Cationic amine surfactants included among those useful in the present invention are disclosed in U.S. Pat. No. 4,275,055, Nachtigal, et al., issued Jun. 23, 1981 (incorporated by reference herein).

Suitable cationic surfactant salts include the halogen, acetate, phosphate, nitrate, citrate, lactate and alkyl sulfate salts.

Nonionic surfactants can also be included in the compositions hereof. Preferably, the nonionic surfactants have an average HLB (Hydrophile-Lipophile Balance) of less than or equal to about 7.

Methods of determining HLB are well known in the art and any of such methods may be used for HLB determination. A description of the HLB System and methods for HLB determination are described in "The HLB System: a time saving guide to emulsifier selection," ICI Americas Inc.; Wilmington, Del.; 1976.

Nonionic surfactants include polyethylene oxide condensates of alkyl phenols (preferably $C_6$–$C_{12}$ alkyl, with a degree of ethoxylation of about 1 to about 6), condensation products of ethylene oxide with the reaction product of propylene oxide and ethylene diamine, condensation products of aliphatic alcohols with ethylene oxide, long chain (i.e., typically $C_{12}$–$C_{22}$) tertiary amine oxides, long chain tertiary phosphine oxides, dialkyl sulfoxides containing one long chain alkyl or hydroxy alkyl radical and one short chain (preferably $C_1$–$C_3$) radical, silicone copolyols, and $C_1$–$C_4$ alkanol amides of acids having a $C_8$–$C_{22}$ acyl moiety.

Ionic Strength Modifier System

Optionally, the compositions of the present invention can contain an effective amount of a non-surface active ionic strength modifier system for reducing the viscosity of the hair spray composition. When used, the ionic strength modifiers will be present in the present compositions at a level of at least about 0.01%, by weight of the composition. The upper limit is dependent upon the maximum amount of the ionic strength modifiers that can be present in the particular compositions hereof such that the hair setting resin remains solubilized or dispersed. As will be understood by those skilled in the art, as the ionic strength of the composition is increased, the resin will eventually fall out of solution, or otherwise no longer remain solubilized or dispersed in the polar liquid carrier. The upper limit of the ionic strength modifier system level will vary depending upon the particular ionic strength modifiers, liquid vehicle, resin, and other ingredients present in the composition. Thus, for example, the maximum amount of the ionic strength modifiers that can be used will tend to be lower for compositions with liquid vehicles containing less water, compared to compositions with more water. Generally, the compositions will comprise about 4%, by weight, or less of the ionic strength modifiers, more generally about 2% or less, and typically about 1% or less. Preferably, the compositions hereof will comprise from about 0.01% to about 0.5%, more preferably from about 0.01% to about 0.1%, of the ionic strength modifier system.

The ionic strength modifier system comprises a mixture of monomeric cations and anions. The ions of the ionic strength modifier system hereof are non-surface active, i.e. they do not significantly reduce surface tension. For purposes hereof, non-surface active shall mean the ions, which at a 0.5% aqueous solution concentration, reduce surface tension by no more than 5.0 dynes/cm2. Generally, the ions of the ionic strength modifier system hereof will be characterized by having, at maximum, four or less carbon atoms per charge, preferably two or less carbon atoms, in any aliphatic chain or straight or branched chain organic heterochain.

The ionic strength modifier system comprises monomeric ions of the type which are products of acid-base reactions. Thus, basic and acidic ions $OH^-$ and $H^+$ do not constitute part of the ionic strength modifier system hereof, although they may be present in the composition. The ions hereof are incorporated into the composition in a form such that they can exist in the composition as free ions, i.e., in dissociated form. It is not necessary that all of the ions added exist in the composition as free ions, but must be at least partially soluble or dissociated in the composition. The ionic strength modifiers can be incorporated into the hair styling compositions, for example, by addition of soluble salts, or by addition of mixtures of acids and bases, or by a combination thereof. It is a necessary aspect of the invention that both anions and cations of the ionic strength modifier system be included in the composition.

Suitable cations for use include, for example, alkali metals, such as lithium, sodium, and potassium, and alkaline-earth metals, such as magnesium, calcium, and strontium. Preferred of the divalent cations is magnesium. Preferred monovalent metal ions are lithium, sodium, and potassium, particularly sodium and potassium. Suitable means of addition to the compositions hereof include, for example, addition as bases, e.g., hydroxides, sodium hydroxide and potassium hydroxide, and such as salts that are soluble in the liquid carrier, e.g. salts of monomeric anions such as those described below.

Other suitable cations include organic ions, such as quaternary ammonium ions and cationic amines, such as ammonium mono-, di-, and tri-ethanolamines, triethylamine, morpholine, aminomethylpropanol (AMP), aminoethylpropanediol, etc. Ammonium and the amines are preferably provided in the forms of salts, such as hydrochloride salts.

Monomeric anions that can be used include halogen ions, such as chloride, fluoride, bromide, and iodide, particularly chloride, sulfate, ethyl sulfate, methyl sulfate, cyclohexyl sulfamate, thiosulfate, toluene sulfonate, xylene sulfonate, citrate, nitrate, bicarbonate, adipate, succinate, saccharinate, benzoate, lactate, borate, isethionate, tartrate, and other monomeric anions that can exist in dissociated form in the hair styling composition. The anions can be added to the compositions hereof, for example, in the form of acids or salts which are at least partially soluble in the liquid vehicle, e.g., sodium or potassium salts of acetate, citrate, nitrate, chloride, sulfate, etc. Preferably, such salts are entirely soluble in the vehicle.

The use of ionic strength modifiers are especially useful in reduced volatile organic solvent compositions, most especially those utilizing silicone macromer-containing polymers.

Hair Styling Compositions

The present invention encompasses a wide variety of hair styling compositions, including hair spray compositions, mousses, and hair setting tonics. In general, the compositions will be flowable, low viscosity compositions that, preferably, are suitable for spray application. Higher viscosity compositions are also contemplated, however.

Hair spray compositions and mousses of the present invention can be dispensed from containers which are aerosol dispensers or pump spray dispensers. Such dispensers, i.e., containers, are well known to those skilled in the art and are commercially available from a variety of manufacturers, including American National Can Corp. and Continental Can Corp.

When the hair spray compositions are to be dispensed from a pressurized aerosol container, a propellant which consists of one or more of the conventionally-known aerosol propellants may be used to propel the compositions. A suitable propellant for use can be generally any liquifiable gas conventionally used for aerosol containers.

Suitable propellants for use are volatile hydrocarbon propellants which can include liquified lower hydrocarbons of 3 to 4 carbon atoms such as propane, butane and isobutane. Other suitable propellants are hydrofluorocarbons such as 1,2-difluoroethane (Hydrofluorocarbon 152A) supplied as Dymel 152A by DuPont. Other examples of propellants are dimethylether, nitrogen, carbon dioxide, nitrous oxide and atmospheric gas.

The hydrocarbons, particularly isobutane, used singly or admixed with other hydrocarbons are preferred.

The aerosol propellant may be mixed with the present compositions and the amount of propellant to be mixed is governed by normal factors well known in the aerosol art. Generally, for liquifiable propellants, the level of propellant is from about 10% to about 60% by weight of the total composition, preferably from about 15% to about 50% by weight of the total composition.

Alternatively, pressurized aerosol dispensers can be used where the propellant is separated from contact with the hair spray composition such as a two compartment can of the type sold under the tradename SEPRO from American National Can Corp.

Other suitable aerosol dispensers are those characterized by the propellant being compressed air which can be filled into the dispenser by means of a pump or equivalent device prior to use. Such dispensers are described in U.S. Pat. No. 4,077,441, Mar. 7, 1978, Olofsson and U.S. Pat. No. 4,850,577, Jul. 25, 1989, TerStege, both incorporated by reference herein, and in U.S. Ser. No. 07/839,648, Gosselin et al., filed Feb. 21, 1992, also incorporated by reference herein. Compressed air aerosol containers suitable for use are also currently marketed by The Procter & Gamble Company under their tradename VIDAL SASSOON AIRSPRAY® hair sprays.

Conventional non-aerosol pump spray dispensers, i.e., atomizers, can also be used.

Other hair styling compositions include tonics and lotions, which are typically dispensed in a conventional bottle or tube, and applied directly to the hair or first dispensed to the hand and then to the hair.

The hair styling formulations of the present invention can optionally contain conventional hair care composition adjuvants. Generally, adjuvants collectively can comprise from about 0.05% to about 5% by weight and preferably from about 0.1% to about 3%, by weight. Such conventional optional adjuvants are well known to those skilled in the art and include in addition to those discussed above, emollients; lubricants and penetrants such as various lanolin compounds; protein hydrolysates and other protein derivatives; ethylene adducts and polyoxyethylene cholesterol; dyes, tints, bleaches, reducing agents and other colorants; pH adjusting agents sunscreens; preservatives; thickening agents (e.g. polymeric thickeners, such as xanthan gum); and perfume.

METHOD OF MAKING

The hair styling compositions of the present invention can be made using conventional formulation and mixing techniques. Preferably, a premix of the silicone grafted polymer and the ethanol is made first. If ethanol is not to be used in the composition, a premix of the polymer with $C_3$ alkanol or water is prepared. The other ingredients can then be added with mixing to provide a homogeneous mixture. It the polymer is neutralized, the neutralizer is preferably added to the premix prior to addition of other ingredients.

METHOD OF USE

The compositions of the present invention are used in conventional ways to provide the hair styling/holding benefits of the present invention. Such method generally involves application of an effective amount of the product to dry, slightly damp, or wet hair before and/or after the hair is arranged to a desired style.. The composition is then dried or allowed to dry. By "effective amount" is meant an amount sufficient to provide the hair hold and style benefits desired considering the length and texture of the hair. In general, from about 0.5 g to about 30 g of product will be applied to the hair, depending upon the particular product formulation, dispenser type, length of hair, and type of hair style.

The following Experimentals and Examples further illustrate embodiments within the scope of the present invention. They are given solely for the purposes of illustration and are not to be construed as limitations of the present invention as many variations of the invention are possible without departing from its spirit and scope.

EXPERIMENTALS

The following synthesis exemplify silicone grafted polymers useful in the present compositions.

Experimental 1: Batch synthesis

Place 20 parts acrylic acid, 60 parts t-butyl acrylate, and 20 parts polysiloxane (10,000 MW) -containing monomer in a flask. Add sufficient ethyl acetate or acetone as the reaction solvent to produce a final monomer concentration of 20%. Purge the vessel with an inert atmosphere, preferably nitrogen or argon. Add initiator, (2,2'-azobis-(2,4-dimethylvaleronitrile)) to a level appropriate for the desires molecular weight. Typically this is in the range of 0.5% to 1.0% by weight relative to the amount of monomer. Purge the vessel with an inert atmosphere, preferably nitrogen or argon. Heat to 60° C. and maintain this temperature for 48 hours while agitating. Terminate the reaction by cooling to room temperature. The polymer is purified by drying off the reaction solvent in an oven, or if acetone is used as the solvent precipitating the polymer, by adding water and then drying the precipitate.

Experimental 2: Semi-continuous synthesis

Place 20 pads acrylic acid, 60 parts t-butyl acrylate, and 30 parts polysiloxane (10,000 MW) -containing monomer in a flask. Add 300 parts ethyl acetate or acetone as the reaction solvent to produce a final monomer concentration of 20%. Purge the vessel with an inert atmosphere, e.g. nitrogen or argon. Add initiator, (2,2'-azobis-(2,4-dimethylvaleronitrile)) as in Experimental 1. Heat to 60° C. and maintain this temperature. After polymerization of these monomers has proceeded about 15 minutes to about 1 hour, e.g. about 30 minutes, add a second monomer charge of 20 parts acrylic acid and 60 parts t-butyl acrylate, to give a final total monomer charge of approximately 40% by weight. Maintain at temperature for 48 hours. Terminate the reaction and purify the polymer as in Experimental 1.

EXAMPLES

Examples 1–6

The following examples represent nonaerosol hairspray compositions of the present invention.

| Component (wt. %) | Example No | | | | | |
|---|---|---|---|---|---|---|
| | 1 | 2 | 3 | 4 | 5 | 6 |
| Silicone Grafted Polymer[1] | 4.00 | 4.00 | 4.50 | 4.50 | 4.50 | 4.50 |
| Isododecane[2] | 3.00 | 3.00 | 3.00 | 3.00 | 5.00 | 5.00 |
| Acetyl triethyl citrate[3] | 0.20 | — | 0.22 | — | — | — |
| Diisopropyl butyl adipate | — | — | — | 0.22 | 0.32 | — |
| Potassium hydroxide | 0.40 | 0.40 | 0.40 | 0.45 | 0.44 | 0.44 |
| Perfume | 0.10 | 0.10 | 0.20 | 0.20 | 0.20 | 0.20 |
| Water | 16.00 | 16.10 | 7.00 | 7.00 | 15.54 | 15.86 |
| Ethanol[4] | 75.30 | 75.50 | 84.62 | 84.63 | 74.00 | 74.00 |

[1] 60% t-butyl acrylate/20% acrylic acid/20% silicone macromer (weight average molecular weight of silicone macromer of about 10,000), having a weight average molecular weight of about 150,000.
[2] PERMETHYL 99A, from Presperse, Inc., South Plainfield, NJ, USA.
[3] CITROFLEX A-2, from Morflex, Inc., Greensboro, NC, USA.
[4] SDA 40 (100% ethanol).

Examples 7–10

The following examples represent aerosol hairspray compositions of the present invention.

| Component (wt. %) | Example No. | | | |
|---|---|---|---|---|
| | 7 | 8 | 9 | 10 |
| Silicone Grafted Polymer[1] | 3.50 | 3.50 | 3.50 | 3.50 |
| Isododecane[2] | 3.00 | 3.00 | 3.00 | 3.00 |
| Acetyl triethyl citrate[3] | 0.18 | 0.18 | — | — |
| Diisopropyl butyl adipate | — | — | — | 0.18 |
| Potassium hydroxide | 0.33 | 0.33 | 0.33 | 0.33 |
| Perfume | 0.10 | 0.10 | 0.10 | 0.10 |
| Water | 5.00 | 20.98 | 5.00 | 5.00 |
| Ethanol[4] | 64.89 | 64.89 | 65.07 | 64.89 |
| Propellant-Isobutane | 7.02 | 7.02 | 7.02 | 7.02 |
| Propellant-Hydrofluorocarbon 152a | 15.98 | — | 15.98 | 15.98 |

[1] 60% t-butyl acrylate/20% acrylic acid/20% silicone macromer (weight average molecular weight of silicone macromer of about 10,000), having a weight average molecular weight of about 150,000.
[2] PERMETHYL 99A, from Presperse, Inc., South Plainfield, NJ, USA.
[3] CITROFLEX A-2, from Morflex, Inc., Greensboro, NC, USA.
[4] SDA 40 (100% ethanol).

In Examples 1–10, the compositions are prepared as described above, by first preparing a polymer premix with the ethanol, neutralizing the polymer with the potassium hydroxide (added as a 45% aqueous solution), then adding sequentially (as applicable) with mixing, water, isododecane, plasticizer, and perfume. Propellants for aerosol compositions are charged to conventional aerosol containers after the remainder of the prepared composition has been added.

Example 11

A hair spray composition, of the present invention, which is suitable for use in pump spray dispensers, is prepared as follows:

| Ingredient | Weight % |
|---|---|
| Ethanol, 200 proof | 75.92% |
| Isopropanol | 10.00% |

| Ingredient | Weight % |
| --- | --- |
| Silicone Grafter Polymer[1] | 3.00% |
| KOH (45%)[2] | 0.88% |
| DRO Water[3] | 7.00% |
| Isododecane | 3.00% |
| Fluorad FC-109[R] (25%)[4] | 0.20% |

[1]60% t-butyl acrylate/20% acrylic acid/20% silicone macromer weight average mw = 10,000, having a weight average molecular weight of about 690,000.
[2]Potassium hydroxide solution, containing 45% potassium hydroxide and 55% water and minors, supplied by Fisher Scientific.
[3]Double reverse osmosis water
[4]Fluorad FC-109[R] supplied by 3M containing 25% potassium fluoroalkyl carboxylates (an anionic fluorosurfactant), 12% propanol, 2% ethanol and 61% water and minors.

The hair spray formulation of Example II is prepared by preparing a premix of the resin in isopropanol. The isopropanol premix is added to the ethanol and then neutralized with the potassium hydroxide solution. Then, a premix of the fluorosurfactants and water is prepared and added to the neutralized premix. Isododecane is then added. Other adjuvants, such as fragrances, may then be added. A magnetic or air driven stirrer is used to mix the ingredients until the resin is dissolved.

Example 12

A hair spray composition, of the present invention, which is suitable for use in pump spray dispensers, is prepared as follows:

| Ingredient | Weight % |
| --- | --- |
| Ethanol, 200 proof | 84.45% |
| Silicone Grafter Polymer[1] | 3.00% |
| KOH (45%) | 0.88% |
| DRO Water | 7.00% |
| Isododecane | 5.00% |
| Zonyl FSK[R] (47%)[2] | 0.11% |

[1]60% t-butyl acrylate/20% acrylic acid/20% silicone macromer weight average mw = 10,000, having a weight average molecular weight of about 690,000/
[2]Zonyl FSK[R] containing 47% fluorosurfactants conforming to the formula $R_fCH_2CH(OCOCH_3)CH_2N^+(CH_3)_2CH_2CO_2^-$ wherein $R_f = F(CF_2CF_2)_{3-8}$ and 53% Acetic Acid and minors, having a zwitterionic character, supplied by DuPont.

This composition is prepared as in Example 11.

Example 13

A hair spray composition, of the present invention, which is suitable for use in pump spray dispensers, is prepared as follows:

| Ingredient | Weight % |
| --- | --- |
| Ethanol, 200 proof | 76.10% |
| Isopropanol | 10.40% |
| Silicone Grafter Polymer[1] | 2.60% |
| KOH (45%) | 0.75% |
| DRO Water | 7.00% |
| Isopar™H (Exxon Chemical)[2] | 3.00% |
| Fluorad FC-120[R] (25%)[3] | 0.10% |
| Zonyl FSK (47%) | 0.05% |

[1]60% t-butyl acrylate/20% acrylic acid/20% silicone macromer weight average mw = 10,000, having a weight average molecular weight of about 800,000.
[2]Isopar™H is a $C_{11-12}$ Isoparaffin
[3]Fluorad FC-120[R] supplied by 3M, having an anionic character and containing 25% mixed ammonium perfluoroalkyl sulfonates, 37.5% ethanol, and 37.5% water and minors.

This composition is prepared as in Example 11, substituting Isopar H for isododecane during processing.

Example 14

A hair spray composition, of the present invention, which is suitable for use in pump spray dispensers, is prepared as follows:

| Ingredient | Weight % |
| --- | --- |
| Ethanol, 200 proof | 75.86% |
| Isopropanol | 10.40% |
| Silicone Grafted Polymer[1] | 2.60% |
| KOH (45%) | 0.69% |
| DRO Water | 7.00% |
| Isopar™L (Exxon Chemical)[2] | 3.00% |
| Fluorad FC-120[R] (25%) | 0.40% |
| Zonyl FSK[R] (47%) | 0.05% |

[1]60% t-butyl acrylate/20% acrylic acid/20% silicone macromer weight average mw = 10,000, having a weight average molecular weight of about 1,700,000.
[2]Isopar™L is a $C_{11-13}$ Isoparaffin This composition is prepared as in Example 13.

Example 15

A hair spray composition, of the present invention, which is suitable for use in pump spray dispensers, is prepared as follows:

| Ingredient | Weight % |
| --- | --- |
| Ethanol, 200 proof | 86.55% |
| Silicone Grafted Polymer[1] | 2.60% |
| KOH (45%) | 0.75% |
| DRO Water | 7.00% |
| Isopar™M(Exxon Chemical)[2] | 3.00% |
| Fluorad FC-135[R] (50%)[3] | 0.10% |

[1]60% t-butyl acrylate/20% acrylic acid/20% silicone macromer weight average mw = 20,000, having a weight average molecular weight of about 800,000.
[2]Isopar™M is a $C_{13-14}$ Isoparaffin
[3]Fluorad FC-135[R] supplied by 3M, having anionic character and containing 25% mixed ammonium perfluoroalkyl sulfonates, 37.5% ethanol and 37.5% water and minors.

This composition is prepared as in Example 13.

What is claimed is:

1. A hair styling composition comprising:
   (a) from about 0.1% to about 15%, by weight, of a silicone grafted adhesive polymer, said polymer being characterized by an organic polymeric backbone having silicone macromers grafted to said backbone;
   (b) from about 0.5% to about 15%, by weight, of hydrocarbon solvent selected from the group consisting of $C_{10}$–$C_{14}$ branched chain hydrocarbons, and mixtures thereof having a boiling point of from about 105° C. to about 260° C.;

(c) a polar solvent phase comprising from about 80% to about 98.9%, by weight of the composition, of a polar solvent selected from the group consisting of water and $C_2$–$C_3$ monohydric alcohols, and mixtures thereof, wherein said composition contains no more than about 15% by weight, of $C_3$ monohydric alcohol;

wherein said organic polymer backbone is soluble in said polar solvent phase, and said silicone macromers of said hair setting polymer are soluble in said hydrocabon solvent and insoluble in said polar solvent.

2. A hair styling composition as in claim 1, wherein said composition comprises:

(a) from about 0.5% to about 8%, by weight, of said silicone grafted polymer;

(b) from about 1% to about 10%, by 10%, by weight, of said hydrocarbon solvent;

(c) from about 85% to about 98%, by weight, of said polar solvent, wherein said composition contains no more than about 12%, by weight, of $C_3$ monohydric alcohol.

3. A hair styling composition as in claim 1, wherein said composition comprises:

(a) from about 1% to about 8%, by weight, of said silicone grafted polymer;

(b) from about 2% to about 8%, by weight, of said hydrocarbon solvent;

(c) from about 80% to about 98.9%, by weight, of said polar solvent, wherein said composition contains no more than about 12%, by weight, of $C_3$ monohydric alcohol and said composition contains at least about 10%, by weight, of water and no more than 80%, by weight, of volatile organic compounds.

4. A hair styling composition as in claim 1, wherein said composition comprises no more than 80% of volatile organic compounds.

5. A hair styling composition as in claim 1, wherein said silicone grafted polymer comprises from about 50% to about 99%, by weight, of non-silicone macromer-containing monomer units and from about 1% to about 50%, by weight of silicone macromer-containing monomer units.

6. A hair styling composition as in claim 1, wherein said silicone grafter polymer comprises from about 60% to about 98%, by weight, of non-silicone macromer-containing monomer units and from about 19% to about 40%, by weight of silicone macromer-containing monomer units.

7. A hair styling composition as in claim 1, wherein said silicone grafted polymer comprises from about 75% to about 95%, by weight, of non-silicone macromer-containing monomer units and from about 2% to about 25%, by weight of silicone macromer-containing monomer units.

8. A hair styling composition as in claim 5, wherein said silicone grafted polymer comprises from about 1% to about 99%, by weight, of hydrophilic monomer units and from about 0% to about 99%, by weight, of hydrophobic monomer units.

9. A hair styling composition as in claim 6, wherein said silicone grafted polymer comprises from about 5% to about 80%, by weight, of hydrophilic monomer units and from about 1% to about 90%, by weight, of hydrophobic monomer units.

10. A hair styling composition as in claim 7, wherein said silicone grafted polymer comprises from about 10% to about 50%, by weight, of hydrophilic monomer units and from about 5% to about 85%, by weight, of hydrophobic monomer units.

11. A hair styling composition as in claim 10, wherein said silicone grafted polymer comprises from about 15% to about 40%, by weight, of hydrophilic monomer units and from about 15% to about 80%, by weight, of hydrophobic monomer units.

12. A hair styling composition as in claim 8, wherein said hydrophilic monomer units are selected from the group consisting of acrylic acid, methacrylic acid, N,N-dimethylacrylamide, dimethyl aminoethyl methacrylate, quaternized dimethylaminoethyl methacrylate, methacrylamide, N-t-butyl acrylamide, maleic acid, maleic anhydride and its half esters, crotonic acid, itaconic acid, acrylamide, acrylate alcohols, hydroxyethyl methacrylate, diallyldimethyl ammonium chloride, vinyl pyrrolidone, vinyl ethers, maleimides, vinyl pyridine, vinyl imidazole, styrene sulfonate, allyl alcohol, vinyl alcohol, vinyl caprolactam, and salts of acids and amines above, and mixtures thereof.

13. A hair styling composition as in claim 12, wherein said hydrophilic monomer units are selected from the group consisting of acrylic acid, N,N-dimethyl acrylamide, dimethylaminoethyl methacrylate, quaternized dimethyl aminoethyl methacrylate, vinyl pyrrolidone, salts of acids and amines thereof, and mixtures thereof.

14. A hair styling composition as in claim 12, wherein said hydrophobic monomer units are selected from the group consisting of acrylic and methacrylic acid esters of $C_1$–$C_{18}$ alcohols, styrene; polystyrene macromer; vinyl acetate; vinyl chloride; vinylidene chloride; vinyl propionate; alpha-methylstyrene; t-butylstyrene; butadiene; cyclohexadiene; ethylene; propylene; vinyl toluene; and mixtures thereof.

15. A hair styling composition as in claim 14, wherein said hydrophobic monomer units are selected from the group consisting of n-butyl methacrylate, isobutyl methacrylate, t-butyl acrylate, t-butyl methacrylate, 2-ethylhexyl methacrylate, methyl methacrylate, and mixtures thereof.

16. A hair styling composition as in claim 15, wherein said hydrophobic monomer units are selected from the group consisting of t-butyl acrylate, t-butyl methacrylate, and mixtures thereof.

17. A hair styling composition as in claim 10, wherein said hydrophilic monomer units are selected from the group consisting of acrylic acid, N,N-dimethyl acrylamide, dimethylaminoethyl methacrylate, quaternized dimethyl aminoethyl methacrylate, vinyl pyrrolidone, salts of acids and amines thereof, and mixtures thereof.

18. A hair styling composition as in claim 17, wherein said hydrophobic monomer units are selected from the group consisting of n-butyl methacrylate, isobutyl methacrylate, t-butyl acrylate, t-butyl methacrylate, 2-ethylhexyl methacrylate, methyl methacrylate, and mixtures thereof.

19. A hair styling composition as in claim 1, wherein said hydrocarbon solvent is selected from the group consisting of saturated $C_{10}$–$C_{14}$ branched chain hydrocarbons, and mixtures thereof.

20. A hair styling composition as in claim 2, wherein said hydrocarbon solvent is selected from the group consisting of $C_{11}$–$C_{13}$ branched chain hydrocarbons.

21. A hair styling composition as in claim 20, wherein said hydrocarbon solvent is isododecane.

22. A Hair styling composition comprising:

(a) from about 0.1% to about 15%, by weight, of a silicone grafted adhesive polymer, said polymer being characterized by an organic polymeric backbone having silicone macromers grafted to said backbone;

(b) from about 0.5% to about 15%, by weight, of a hydrocarbon solvent selected from the group consisting of $C_{10}$–$C_{14}$ branched chain hydrocarbons, and mixtures thereof having a boiling point of from about 105° C. to about 260° C.;

(c) a polar solvent phase comprising from about 80% to about 98.9%, by weight of the composition, of a polar solvent selected from the group consisting of water and $C_2$–$C_3$ monohydric alcohols, and mixtures thereof, wherein said composition contains no more than about 15%, by weight, of $C_3$ monohydric alcohol;

(d) from about 0.025% to about 2%, by weight, of a plasticizer selected from the group consisting of acetyl tri-$C_2$–$C_8$alkyl citrates, and mixtures thereof;

wherein said organic polymer backbone is soluble in said polar solvent phase, and said silicone macromers of said hair setting polymer are soluble in said hydrocarbon solvent and insoluble in said polar solvent.

23. A hair styling composition as in claim 1, wherein said hydrocarbon solvent is selected from the group consisting of saturated $C_{10}$–$C_{14}$ branched chain hydrocarbons, and mixtures thereof.

24. A hair styling composition as in claim 23, wherein said plasticizer is acetyl triethyl citrate.

25. A hair styling composition as in claim 24, wherein said hydrocarbon solvent is a $C_{11}$–$C_{13}$ branched chain hydrocarbon.

26. A hair styling composition as in claim 25, wherein said hydrocarbon solvent is a $C_{12}$ branched chain hydrocarbon.

27. A hair styling composition as in claim 26, wherein said hydrocarbon solvent is isododecane.

28. A hair spray composition comprising a composition as in claim 1 disposed within a hair spray dispenser.

29. A hair spray composition comprising a composition as in claim 2 disposed within a hair spray dispenser.

30. A hair spray composition comprising a composition as in claim 14 disposed within a hair spray dispenser.

* * * * *